United States Patent [19]

Ryer et al.

[11] 4,176,073
[45] Nov. 27, 1979

[54] MOLYBDENUM COMPLEXES OF LACTONE OXAZOLINE DISPERSANTS AS FRICTION REDUCING ANTIWEAR ADDITIVES FOR LUBRICATING OILS

[75] Inventors: Jack Ryer, East Brunswick; Esther D. Winans, Colonia; Stanley J. Brois, Westfield; Antonio Gutierre, Mercerville, all of N.J.

[73] Assignee: Exxon Research & Engineering Co., Florham Park, N.J.

[21] Appl. No.: 943,206

[22] Filed: Sep. 18, 1978

[51] Int. Cl.$^2$ .................... C10M 1/54; C10M 1/48; C10L 1/30; C07F 11/00
[52] U.S. Cl. .................... 252/32.7 E; 44/63; 44/68; 252/49.7; 548/110; 548/101; 548/237
[58] Field of Search .................... 252/32.7 E, 49.7; 260/299; 44/63, 68

[56] References Cited

U.S. PATENT DOCUMENTS

| | | | |
|---|---|---|---|
| 2,450,806 | 10/1948 | McCarthy | 252/49.7 |
| 2,450,807 | 10/1948 | McCarthy | 252/49.7 |
| 4,035,309 | 7/1977 | Brois | 252/49.7 |
| 4,062,786 | 12/1977 | Brois et al. | 252/51.5 R |
| 4,102,798 | 7/1978 | Ryer et al. | 252/51.5 A |

FOREIGN PATENT DOCUMENTS 882295 11/1961 United Kingdom .................... 252/49.7

*Primary Examiner*—Irving Vaughn
*Attorney, Agent, or Firm*—Roland A. Dexter

[57] ABSTRACT

A molybdenum complex of a lactone oxazoline dispersant, preferably an oil-soluble lactone oxazoline obtained as a reaction product of hydrocarbyl substituted lactone carboxylic acids, for example, polybutyl lactone carboxylic acid, with 2,2-disubstituted-2-amino-1-alkanols, such as tris-(hydroxymethyl) aminomethane (THAM), and their derivatives are useful additives in lubricating oils since both the sludge dispersant and antifriction properties of said oil are enhanced.

17 Claims, No Drawings

MOLYBDENUM COMPLEXES OF LACTONE OXAZOLINE DISPERSANTS AS FRICTION REDUCING ANTIWEAR ADDITIVES FOR LUBRICATING OILS

BACKGROUND OF THE INVENTION

The present invention concerns oil-soluble molybdenum complexes of lactone oxazoline dispersants, their method of preparation, and the utility of said molybdenum containing dispersants as lubricating oil additives, which markedly improve the sludge dispersancy-friction reducing properties of lubricating oils employed for crankcase lubrication of internal combustion engines.

There are two principle environments which are encountered by automotive crankcase lubricants, i.e. cyclical high and low temperatures from stop-and-go driving and continuous high temperatures from extended operation of the automobile over long distances. Each of these environments provokes the presence in the lubricant of varying proportions of foreign particles such as dirt, soot, water and decomposition products resulting from breakdown of the oil. This foreign matter appears responsible for the deposition of a mayonnaise-like sludge which circulates with the oil.

During the past decade, ashless sludge dispersants have become increasingly important, primarily in improving the performance of lubricants in keeping the engine clean of deposits and permitting extended crankcase oil drain periods while avoiding the undesirable environmental impact of the earlier used metal-containing additives.

Included within the published ashless sludge dispersants are the oil-soluble oxazolines such as are disclosed in United Kingdom Specifications No. 1,483,681-2 and the oil-soluble lactone oxazolines as taught in U.S. Pat. No. 4,062,786. These dispersants are characterized by at least one oxazoline and stated to be useful for various functions, such as antirust agents, detergents, or dispersants for oleaginous compositions including lube oil, gasoline, turbine oils and oils for drilling applications.

In the operation of an internal combustion engine, there are many "Boundary Lubrication" conditions where two rubbing surfaces must be lubricated, or otherwise protected, so as to prevent wear and to insure continued movement. Moreover, where, as in most cases, friction between the two surfaces will increase the power required to effect movement and where the movement is an integral part of an energy conversion system, it is most desirable to effect the lubrication in a manner which will minimize this friction and/or reduce wear. As is also well known, both wear and friction can be reduced, with various degrees of success, through the addition of a suitable additive or combination thereof, to a natural or synthetic lubricant. Similarly, continued movement can be insured, again with varying degrees of success, through the addition of one or more appropriate additives.

While there are many known lubricant additives which may be classified as antiwear, antifriction and extreme pressure agents and some may in fact satisfy more than one of these functions as well as provide other useful functions but rarely if ever dispersancy, it is also known that many of these additives act in a different physical or chemical manner and often compete with one another, e.g. they may compete for the surface of the moving metal parts which are subjected to lubrication. Accordingly, extreme care must be exercised in the selection of these additives to insure compatibility and effectiveness.

The metal dihydrocarbyl dithiophosphates, e.g. the zinc dialkyl dithiophosphates, are one of the additives which are known to exhibit antioxidant and antiwear properties. While they afford excellent oxidation resistances and exhibit superior antiwear properties, it has heretofore been believed that the same increases or significantly limits their ability to decrease friction between moving surfaces. As a result, compositions containing zinc dialkyl dithiophosphates were not believed to provide the most desirable lubricity and, in turn, it was believed that use of compositions containing the same would lead to significant energy losses in overcoming friction even when antifriction agents are included in the composition.

Known ways to solve the problem of energy losses due to high friction in crankcase lubrication include the use of synthetic ester base oils which are expensive and the use of insoluble molybdenum sulfide and graphite dispersions which have the disadvantage of giving the oil composition a black or hazy appearance. It would be desirable then to provide oil-soluble molybdenum compounds and thus overcome the disadvantage. Oil-soluble molybdenum additives taught as useful in lubricating oils include the molybdates of organic nitrogen bases obtained from heating an aqueous solution of molybdic acid and an aliphatic amine or heterocyclic nitrogen base (see U.S. Pat. No. 3,144,712).

The practical exploitation of various types of molybdenum compounds and complexes as lubricant additives has been hindered not only by their insolubility and/or corrosiveness but also by low thermal stability.

SUMMARY OF THE INVENTION

It has now been discovered that lactone oxazoline dispersants can be reacted with a source of molybdenum to provide a molybdenum-containing ashless dispersant of improved thermal stability in hydrocarbons, preferably lubricating oils and having the property of importing enhanced lubricity to said lubricating oil. This has been accomplished by use of an aqueous-non-aqueous reaction medium. The operational embodiment of the invention thus is a lubricating oil composition comprising a major proportion of mineral oil and a minor but at friction reducing amount of an oil-soluble molybdenum-containing lactone oxazoline lubricating oil dispersant, said dispersant having from 0.5 to 20 wt.% molybdenum based on the weight of said dispersant and further characterized by from one to two lactone rings, one to two oxazoline rings and at least one substantially saturated hydrocarbon group containing at least about 50 carbon atoms.

These materials are prepared from lactone oxazoline dispersants by reaction of said dispersant with an inorganic molybdenum compound in a binary solvent system comprising an aqueous component of the class consisting of water and ammonium hydroxide and a non-aqueous component such as mineral oil, tetrahydrofuran (THF) or a hydrocarbon boiling between 70° and 250° C. The volume ratio of aqueous to non-aqueous component ranges from 1:1000 to 1:1, preferably 1:100 to 1:4, optimally 1:10. In the context of this invention, the aqueous component can be considered a promoter for the molybdation of the lactone oxazoline dispersant. Thus, for the purposes of this discussion, both the water and the ammonium hydroxide could be defined as an essential promoter of molybdation in a non-aqueous reaction medium.

It has now been further discovered that a stable molybdenum complex can be obtained with little if any destruction of the ashless dispersant when complexing is effected at a temperature of 40° C. to 250° C., preferably from 50° to 200° C., in said binary solvent system.

In accordance with the present invention, it is preferred that the lubricity enhancing, i.e. friction reducing, additive is present in the mineral oil in an amount to provide from about 0.01 to 2.0, preferably 0.02–1.0 and optimally 0.05–0.5 weight percent molybdenum in said oil. All weight percent being based on the total weight of the lubricating composition.

In preferred form, the molybdenum complex is that of a lactone-oxazoline dispersant derived from the reaction of one mole of a $C_8$ to $C_{400}$ hydrocarbon substituted lactone acid material such as poly(isobutenyl) lactone acid wherein said hydrocarbyl substituent e.g. the poly(isobutenyl) group has a $(\overline{M}_n)$ ranging from about 700 to 5,600, optimally from about 900 to 1600 with one mole equivalent of a 2,2-disubstituted-2-amino-1-alkanol having 2 to 3 hydroxy groups and containing a total of 4 to 8 carbon atoms usefully by heating at a temperature of from 100° C. to 240° C. until cessation of water evolution; said additive being complexed with from 1 to 2 molar equivalents of molybdic oxide, i.e. $MoO_3$ and containing from 0.5 to 20, preferably 2 to 10, optimally 5, wt.% molybdenum.

DETAILED DESCRIPTION OF THE INVENTION

Generally the hydrocarbyl substituted dicarboxylic acid material, i.e., acid or anhydride, or ester which is used to produce the lactone oxazoline dispersants for complexing with molybdenum includes alpha-beta unsaturated $C_4$ to $C_{10}$ dicarboxylic acid, or anhydrides or esters thereof, such as fumaric acid, itaconic acid, maleic acid, maleic anhydride, chloromaleic acid, dimethyl fumarate, etc., which are substituted with a hydrocarbyl group, usefully a hydrocarbon chain containing at least 50 carbons (branched or unbranched) and includes long hydrocarbon chains, generally an olefin polymer chain.

In general, these hydrocarbyl substituted dicarboxylic acid materials and their preparation are well known in the art, for example see U.S. Pat. Nos. 3,219,666; 3,172,892; 3,272,746; the aforementioned prior art patents; as well as being commercially available, e.g., polyisobutylene succinic anhydride.

The dicarboxylic acid material can be illustrated by an alkenyl substituted anhydride which may contain a single alkenyl radical or a mixture of alkenyl radicals variously bonded to the cyclic succinic anhydride group with the alkenyl substituent containing from 8 to 400 carbons and preferably from 50 to 300 carbons. The anhydrides can be obtained by well-known methods, such as the Ene reaction between an olefin and maleic anhydride or halo-succinic anhydride or succinic ester (U.S. Pat. No. 2,568,876).

Suitable olefins include octene, decene, dodecene, tetradecene, hexadecene, octadecene, eicosene, and polymers of propylene, butene, isobutene, pentene, decene and the like, and halogen-containing olefins. The olefins may also contain cycloalkyl and aromatic groups.

With 2-chloromaleic anhydride and related acylating agents, alkenylmaleic anhydride reactants are formed. Derivatization of these reactants also afford useful oxazoline products which can be molybdated.

Preferred olefin polymers for reaction with the unsaturated dicarboxylic acids are polymers comprising a major molar amount of $C_2$ to $C_5$ monoolefin, e.g., ethylene, propylene, butylene, isobutylene and pentene. The polymers can be homopolymers such as polyisobutylene, as well as copolymers of two or more of such olefins such as copolymers of: ethylene and propylene; butylene and isobutylene; propylene and isobutylene; etc. Other copolymers include those in which a minor amount of the copolymer monomers, e.g., 1 to 20 mole % is a $C_4$ to $C_{18}$ non-conjugated diolefin, e.g., a copolymer of isobutylene and butadiene; or a copolymer of ethylene, propylene and 1,4-hexadiene; etc.

The olefin polymers will usually have $(\overline{M}_n)$s within the range of about 700 and about 6,000, more usually between about 900 and about 5,600. Particularly useful olefin polymers have $(\overline{M}_n)$s of about 1200 to 5000 with approximately one terminal double bond per polymer chain. An especially valuable starting material for a highly potent dispersant additive are polyalkenes e.g., polyisobutylene, having about 90 carbons.

LACTONE OXAZOLINE DISPERSANT

Generally, useful lactone oxazoline reaction products and their methods of preparation are fully described in U.S. Pat. No. 4,062,786 which is fully incorporated herein by reference thereto. This lactone oxazoline dispersant can be characterized in part as a reaction product obtained from heating together an equimolar mixture of a hetero or non-hetero hydrocarbon-substituted lactone acid material selected from the group consisting of acids, amides and esters, and a 2,2-disubstituted-2-amino-1-alkanol having 1 to 3 hydroxy groups and containing a total of 4 to 3 hydroxy groups and containing a total of 4 to 8 carbons at a temperature of from 100°–240° C. until infrared absorption for oxazoline is maximal indicating completion of the oxazoline reaction. These reaction products can be represented in part by the formula:

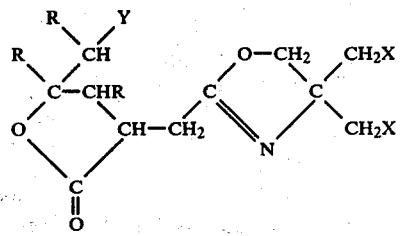

wherein R is selected from the group consisting of hydrogen and alkyl radicals containing from 1 to 400 or more carbons, X is selected from the group consisting of an alkyl or hydroxy alkyl group and at least one of the X substituents and preferably both of the X substituents being a hydroxy alkyl group of the structure $-(CH_2)_n-OH$ where n is 1 to 3 and Y is selected from the group consisting of hydrogen, hydroxyl, sulfo, alkylthio (TS—), alkyldithio (TSS—), and a sulfur bridge, e.g., —S— and —S—S—, joining two lactone oxazoline units together as depicted below wherein z is a number ranging from 1 to 4 and T is defined hereafter as containing 1 to 50, preferably 2 to 20 carbons.

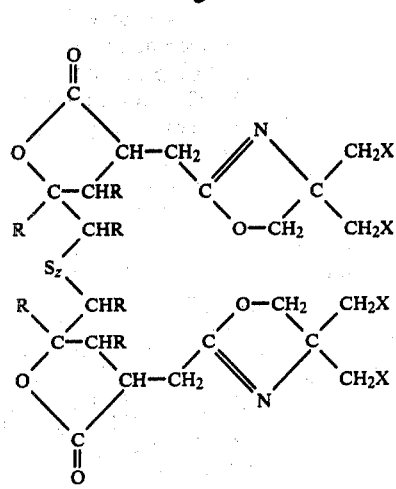

Preferred herein is polyisobutyl lactone oxazoline of number average molecular weight ranging from about 400 to 100,000 prepared by the reaction of equimolar proportions of polyisobutyl lactone carboxylic acid with tris-[hydroxymethyl] aminomethane (THAM) at a temperature from about 100°–240° C. preferably 150°–180° C. until two moles of $H_2O$ per mole of reactant is removed from the reaction.

The lactone oxazoline dispersants are readily prepared by lactonization of an alkenyl succinic acid analogue obtained via the Ene reaction of an olefin with an alpha-beta unsaturated $C_4$ to $C_{10}$ dicarboxylic acid, or anhydrides or esters thereof, such as fumaric acid, itaconic acid, maleic acid, maleic anhydride, dimethyl fumarate, etc.

These hydrocarbon soluble dispersants have at least 8 carbons in the substantially saturated aliphatic hydrocarbyl group and a carboxylic acid group of the dicarboxylic acid material converted into a lactone ring and another carboxylic acid group converted into an oxazoline ring as a result of the reaction of at least equimolar amounts of said hydrocarbon substituted dicarboxylic acid lactone material and a 2,2-disubstituted-2-amino-1-alkanol having 1 to 3 hydroxy groups and containing a total of 4 to 8 carbons, said amino-alkanol preferably having the formula:

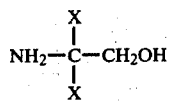

wherein X is alkyl or hydroxy alkyl, said alkyl groups having 1 to 3 carbon atoms, and at least one of said X is a hydroxy alkyl group of the structure $-(CH_2)_nOH$ where n is 1 to 3.

Since it is possible to use alkenyl substituents with the double bond in the 1, 2, or 3-position or even double bonds further out on the hydrocarbyl chain and the size of the lactone ring formed will depend upon, inter alia, the position of the double bond, and which carboxylic acid group participates in the lactone forming reaction, both 5- and 6-ring (or larger ring) lactones are produced and can be used in this invention.

The lactone oxazoline dispersant reagent can include the presence of certain heteroatoms adjacent to the lactone oxazoling ring combination to provide the lactone oxazoline system with other desirable properties such as antioxidation and anticorrosion activity. It is possible to introduce hydroxyl, thiyl, sulfide, sulfoxide, sulfone and sulfo groups adjacent to the lactone oxazoline functions by:

(a) the addition of peracids, hydrocarbyl peroxides or aqueous hydrogen peroxide to alkenyl succinic acid, hemiester or amide reagents or (b) the epoxidation of alkenyl succinic anhydride, with peracids gives epoxy anhydrides which can react with (1) water, alcohols or amines to generate the desired hydroxy-substituted lactone reactants or (2) directly with THAM to give the lactone oxazoline end products, or (c) thiyl substituted lactones prepared via (1) thiol-induced scission of epoxy anhydrides or via (2) sulfenyl halide addition to the double bond in alkenyl succinic acids or esters followed by lactonization via an internal displacement of halide.

Oxidation of the mono-thio-bis-lactones with peroxides can yield both sulfoxides and sulfones. In the case of the dithio-bis-lactones, oxidation affords sulfo-containing lactones. Typical of a hetero substituted lactone oxazoline is mono- or dithio-bis-(polyisobutyl lactone acid).

The amino alcohol used to react with the lactone to provide the oxazoline ring is a 2,2-disubstituted-2-amino-1-alkanol containing a total of 4 to 8 carbon atoms which was earlier discussed.

Examples of such 2,2-disubstituted amino-alkanols, include 2-amino-2-methyl-1,3-propanediol, 2-amino-2-(hydroxymethyl)-1,3-propanediol (also known as tris(-hydroxymethyl) aminomethane or THAM), 2-amino-2-ethyl-1,3-propanediol, etc. Because of its effectiveness, availability and cost, the THAM is particularly preferred. It is to be noted that other amino alcohols such as ethanolamine, propanolamine and butanolamine which lack the 2,2-disubstitution, do not afford the oxazoline product. The requisite ($\overline{M}_n$) ranges of these products have already been specified.

The formation of the preferred oxazoline dispersants in high yield, can be effected by adding about 1.0 (to obtain the monoxazoline) to about 2 (to obtain the bisoxazoline) mole equivalent of the aforesaid 2,2-disubstituted-2-amino-1-alkanol per mole equivalent of the dicarboxylic acid material, with or without an inert diluent, and heating the mixture at 100°–240° C., preferably 160°–205° C., optimally 170°–190° C. for ½ to 24, more usually 2 to 8 hours, until the reaction is complete.

Completion of the oxazoline reaction can be readily ascertained by using periodic infrared spectral analysis for following oxazoline formation (oxazoline peak forms at 6.0 microns), to its maximum absorption at 6 microns.

Although not necessary, the presence of small amounts, such as 0.01 to 2 wt.%, preferably 0.1 to 1 wt.% based on the weight of the reactants, of a metal salt e.g. zinc acetate can be used in the reaction mixture as a catalyst.

Inert solvents which may be used in the oxazoline reaction include hydrocarbon oils, e.g., mineral lubricating oil, kerosene, neutral mineral oils, xylene, halogenated hydrocarbons, e.g., carbon tetrachloride, dichlorobenzene, tetrahydrofuran, etc. Such solvents can be used in molybdation condensation or complexing reaction with said oxazoline dispersant.

While not known with complete certainty, it is believed that the reaction of the alkyl lactone material, e.g., a substituted lactone acid, ester or amide with the amino alcohol of the invention, e.g., about 1.5 to 2 molar equivalents of 2,2-disubstituted-2-aminomethanol such as tris-hydroxymethylaminomethane (THAM), gives lactone oxazoling ring structure.

OIL-SOLUBLE BORATED OXAZOLINE DISPERSANTS

It is possible to molybdate either the lactone oxazoline dispersant or its borated derivative as is described in U.S. Pat. application Ser. No. 763,545, U.S. Pat. No. 4,116,876, filed Jan. 28, 1977 (of common assignee with this application) by reaction with a molybdenum source.

To further enhance the dispersancy of oxazoline dispersants, the said dispersant, e.g. the alkyl lactone oxazoline, is readily borated by treating said lactone oxazoline dispersant with a boron compound selected from the class consisting of boron oxide, boron halides, boron acids and esters of boron acids in a molar ratio of 1:1 to 1:2 of lactone oxazoline dispersant to boron compound.

Borating is readily carried by adding from about 1 to 3 wt.% (based on the weight of said oxazoline compound) of said boron compound, preferably boric acid which is most usually added as a slurry to said lactone oxazoline dispersant and heating with stirring and at above about 60° C. preferably 80° C. to 200° C. for from 1 to 5 hours followed by nitrogen stripping at said temperature ranges and filtration if desired.

The resulting borated lactone oxazolines contain from about 0.1 to 2.0, preferably 0.2 to 0.8, wt.% boron based on the total weight of the borated lactone oxazoline compound. The boron, which appears to be in the reactant dispersant as dehydrated boric acid polymers (primarily $HBO_2)_3$), attaches chemically to the dispersant and appears not displaced in the molybdenumization step.

Oxazoline formation from the dicarboxylic acid material is usefully carried as a solution reaction with the dicarboxylic acid material, e.g. polyisobutenylsuccinic anhydride dissolved in a solvent such as mineral oil to which the other reactant is added. The formation of the oxazoline dispersants in high yield can be effected by adding from about 1 to 1.5 molar proportions of said amino alkanol per molar proportion of the lactone acid and thereafter heating the system within the appropriate temperature range until the appropriate amount of water of reaction is evolved. Typically the solvent mineral oil is adjusted so that it constitutes 50% weight of the final lactone oxazoline dispersant solution. This solution can be readily used for boration as described.

MOLYBDENUM SOURCE

The source of molybdenum is a molybdenum oxygen or sulfur-containing compound capable of complexing with the ashless dispersant to provide a thermally stable molybdenum complex containing from about 0.5 to 20, preferably 2 to 10, optimally about 5 wt.% molybdenum based on the total weight of said complex. The sources of molybdenum include molybdic trioxide (preferred) also known as molybdic anhydride, ammonium thiomolybdate, ammonium bismolybdate, molybdenum halides, and ammonium heptamolybdate tetrahydrate.

METHOD OF PREPARING THE COMPLEX

The molybdenum oxazoline complex is substantially the product of a binary solution reaction between 1-3 moles of lactone oxazoline dispersant (either the borated or non-borated) and 1 mole of molybdenum metal derived from the molybdenum source. The reaction is readily carried out by reaction at an elevated temperature of from 40° C. to 250° C., preferably 50° C. to 200° C. optimally 60° C. to 180° C. said reaction and stabilize the product complex. The reaction is carried out in a binary solution system wherein water is present (either as water or ammonium hydroxide) along with a non-aqueous component such as tetrahydrofuran (THF) or a hydrocarbon boiling between 70° C. and 250° C. and as preferred a second non-aqueous component which is a higher boiling point hydrocarbon as mineral oil. A highly useful reaction system is 1 to 20% water, ammonium hydroxide and mixtures thereof, 20 to 60% mineral oil and the balance xylene or toluene.

The reaction is carried out over a period of from about 4 to 20, preferably 6 to 12, hours in order to suitably stabilize the complex after which the binary solvents are generally removed and the complex dissolved in mineral oil for ease of handling.

Carrying out the organo molybdenum complexing reaction in a binary solvent system wherein one part by weight water or ammonium hydroxide per 1 to 1000 parts by weight of said lower boiling hydrocarbon provides a number of benefits over a reaction without solvent or in a light aromatic solvent such as toluene or a light hydrocarbon oil, e.g. mineral oil including: faster reaction time; completion of reaction to a stabilized molybdenum complex at a lower temperature; and, an additive product solution which when added to lubricating oil provides both enhanced friction reduction and sludge dispersancy.

SULFUR DONORS

The hydrocarbon-soluble molybdenum complexes of oxazoline dispersants provide not only dispersancy for lubricating oils but enhanced lubricity as well as when used in combination with an active sulfur donor which can be defined as a compound which when used in admixture with the sant-molybdenum complex reduces the coefficient of friction at least about 10% relative to that provided by the complex alone. The active sulfur donor is present in an amount of from about 0.1 to 10, preferably 0.2 to 2, parts by weight per part by weight of molybdenum complex.

Illustrative of active sulfur donors are metal dihydrocarbyl dithiophosphates and the corresponding precursor esters, phosphosulfurized pinenes, sulfurized olefins and hydrocarbons, sulfurized fatty esters and sulfurized alkyl phenols.

Preferred are the zinc dihydrocarbyl dithiophosphates which are salts of dihydrocarbyl esters of dithiophosphoric acids and may be represented by the following formula:

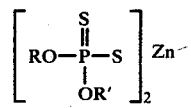

wherein R and R' may be the same or different hydrocarbyl radicals containing from 1 to 18 and preferably 2 to 12 carbon atoms and including radicals such as alkyl, alkenyl, aryl, aralkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, tert-butyl, amyl n-hexyl, i-hexyl, n-heptyl, n-octyl decyl, dodecyl, octadecyl, 2-ethylhexyl, phenyl, butylphenyl, cyclohexyl, methylcyclopentyl, propenyl, butenyl, etc. In order to obtain oil solubility, the total number of carbon atoms in the dithiophosphoric acid will average about 5 or greater.

The zinc dihydrocarbyl dithiophosphates which are useful as the coadditive, i.e. sulfur donor of the present invention may be prepared in accordance with known techniques by first esterifying a dithiophosphoric acid usually by reaction of an alcohol or phenol with $P_2S_5$ and then neutralizing the dithiophosphoric acid ester with a suitable zinc compound such as zinc oxide.

In general, the zinc dihydrocarbyl dithiophosphate will be used in the lubricating composition at a concentration within the range of about 0.01 to about 5 parts by weight per 100 parts of lubricating oil and preferably from about 0.5 to about 1.5. This is adequate for sulfur donation whereby the lubricity enhancement of the lubricating oil composition by the coadditive combination is realized.

As noted earlier, an equally suitable active sulfur donor is the dihydrocarbyl esters of dithiophosphoric acid which may be represented by the formula:

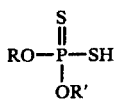

where R and R' are as previously defined. Particularly useful is the dibutylphenyl dithiophosphate.

The phosphorosulfurized terpenes as represented by pinene, dipenene, allo-ocimene, etc., are another group of dithiophosphate diesters which are active sulfur donors. Of the terpenes, the bicyclic pinene is preferred. The phosphosulfurized terpene is readily obtained by reaction of about one mole of diester of thiophosphoric acid and one mole of pinene at a temperature of at least 100° C., e.g. 100° C. to 200° C. The preferred active sulfur donor can be characterized as the bornyl ester of dihydrocarbyl ($C_2-C_{20}$) dithiophosphoric acids (as shown in U.S. Pat. No. 2,689,258).

The sulfurized olefins and hydrocarbons are further esters of thiophosphoric acids which are useful sulfur donors. These esters are achieved by reaction with olefins such as ethylene, propylene, isobutylene, decene, dodecene, octadecene, etc., olefin polymers of molecular weight ranging from 100 to 50,000 such as ethylene, propylene, isobutylene, etc., aromatics such as benzene, naphthylene, toluene, xylene, etc., petroleum fractions and condensation products of halogenated aliphatic hydrocarbons with aromatic compounds, e.g. wax naphthalene (see U.S. Pat. No. 2,804,431).

The sulfurized fatty esters are another subclass of esters which are active sulfur donors. These products are readily obtained from the reaction of $P_2S_5$ and aliphatic alcohols usefully having from about 8 to 22 carbons obtained from natural sources including linoleic, palmolitic, behenic, stearic, palmitic, lauric, capric, etc., as well as mixtures obtained from vegetable and animal oils such as tall oil.

The sulfurized alkyl phenols are generally $C_4$ to $C_{20}$ alkyl phenol sulfides. These sulfurized alkyl phenols are readily produced by sulfurizing an alkyl phenol with a sulfur halide or elemental sulfur.

OTHER ADDITIVES FOR LUBRICATING COMPOSITIONS

In addition to the molybdenum complex of the lactone oxazoline dispersant and active sulfur donor, the lubricating oil composition may contain other well-known lubricating oil additives to provide trouble-free operation of the lubricated equipment, such as ashless dispersants, metallic detergents, supplemental oxidation and corrosion inhibitors, extreme pressure agents, rust inhibitors, pour point depressants, viscosity index improvers, etc.

1. ASHLESS DISPERSANTS

As used herein, the terminology "ashless dispersant" in describing both the reactant and the additive is intended to describe the now well-known class of non-metal-containing oil-soluble polymeric additives or the acyl derivatives of relatively high molecular weight carboxylic acids which are capable of dispersing contaminants and the like in hydrocarbons such as lubricating oils. The carboxylic acids may be mono- or polycarboxylic acids and they are generally characterized by substantially hydrocarbon constituents containing an average of 50 to 250 aliphatic carbon atoms.

A preferred class of ashless dispersants are the nitrogen-containing dispersant additives which are generally known in the art as sludge dispersants for crankcase motor oils. These dispersants include mineral oil-soluble salts, amides, imides and esters made from high molecular weight mono- and dicarboxylic acids (and where they exist the corresponding acid anhydrides) and various amines of nitrogen-containing materials having amino nitrogen or heterocyclic nitrogen and at least one amido or hydroxy group capable of salt, amide, imide or ester formation. Usually, these dispersants are made by condensing a monocarboxylic acid or a dicarboxylic acid or anhydride, preferably a succinic acid producing material such as alkenyl succinic anhydride, with an amine or alkylene polyamine. Usually, the molar ratio of acid or anhydride to amine is between 1:1 to 5:1, e.g. 1 mole of $C_{10}$—$C_{100}$ polyisobutenyl succinic anhydride to 2 moles of tetraethylene pentamine.

Primarily because of its ready availability and low cost, the hydrocarbon portion of the mono-, or dicarboxylic acid or anhydride is preferably derived from a polymer of a $C_2$ to $C_5$ monoolefin, said polymer generally having between 50 and 250 carbon atoms. A particularly preferred polymer is polyisobutylene.

Polyalkyleneamines are usually used to make the non-metal-containing dispersant. These polyalkyleneamines include those represented by the general formula:

wherein n is 2 to 3 and m is a number from 0 to 10. Specific compounds coming within the formula include diethylenetriamine, tetraethylenepentamine, dipropylenetriamine, octaethylenenonamine, and tetrapropylenepentamine; N,N-di-(2-aminoethyl) ethylenediamine may also be used. Other aliphatic polyamino compounds that may be used are N-aminoalkylpiperazines, e.g. N-(2-aminoethyl) piperazine. Mixtures of alkylene polyamines approximating tetraethylene pentamine are commercially available, e.g. Dow E-100 sold by Dow Chemical Company of Midland, Mich.

Representative dispersants are formed by reacting about one molar amount of polyisobutenyl succinic anhydride with from about one to about two molar amounts of tetraethylene pentamine or with from about 0.5 to 1 moles of a polyol, e.g. pentaerythritol.

It is possible to modify the ashless dispersants generally by the addition of metals such as boron in order to enhance the dispersancy of the additive. This is readily accomplished by adding boric acid to the reaction mixture after the imidation or esterification is substantially complete and heating the mixture at temperatures of 100° to 150° C. for a few hours.

2. OTHER ADDITIVES

Detergents useful in conjunction with dispersants, preferably the ashless type, include normal, basic or overbased metal, e.g. calcium, magnesium, etc., salts of petroleum naphthenic acids, petroleum sulfonic acids, alkyl benzene sulfonic acids, oil-soluble fatty acids, alkyl salicyclic acids, alkylene-bis-phenols, and hydrolyzed phosphorosulfurized polyolefins.

Oxidation inhibitors include hindered phenols, e.g. 2,6-ditert. butyl para-cresol, amines, sulfurized phenols and alkyl phenothiazines.

Pour point depressants include wax alkylated aromatic hydrocarbons, olefin polymers and copolymers, acrylate and methacrylate polymers and copolymers.

Viscosity Index Improvers include olefin polymers such as polybutene, ethylene-propylene copolymers, hydrogenated polymers and copolymers and terpolymers of styrene with isoprene and/or butadiene, polymers of alkyl acrylates or alkyl methacrylates, copolymers of alkyl methacrylates with N-vinyl pyrollidone or dimethylaminoalkyl methacrylate, post-grafted polymers of ethylene-propylene with an active monomer such as maleic anhydride which may be further reacted with an alcohol or an alkylene polyamine, styrene/maleic anhydride polymers post-reacted with alcohols and amines, etc.

The hydrocarbons in which the additive combination of the invention is most effective are mineral oils having a viscosity as measured by ASTM D-445 of from about 2 to 40, preferably 5 to 20 centistokes at 99° C.

If the molybdenum-containing lactone oxazoline dispersant is used as an additive concentrate, the concentrate may consist essentially of from about 5 to 80 weight percent of molybdenum containing dispersant, based on the total weight of said concentrate, the remainder being a suitable solvent such as kerosene, mineral oil, synthetic oil and a naphtha or the like. The preferred concentrate contains about 10-60 weight percent of the additive combination in the solvent.

Whether the molybdenized lactone oxazoline dispersant is used alone or in combination with other additives, its concentration may vary appreciably with the particular application. For example, when the said molybdenum containing dispersants are used alone in a fuel such as gasoline, the concentration of the additive ranges from 1 to 1000, preferably 5–50 parts per million, based on the total weight of the gasoline. In a lubricant, however, it is used from about 0.1 to 20 preferably 0.5–5% based on the total weight of the oil.

The invention will be further understood by reference to the following Examples which illustrate a preferred form of the invention and compares the same with different, though similar compositions.

The following Examples illustrate more clearly the compositions of the present invention. However, these illustrations are not to be interpreted as specific limitations on this invention.

EXAMPLE 1

224 grams of a 50 wt.% mineral oil solution of a polyisobutyl lactone oxazoline having a ($\overline{M}_n$) of 1120 (0.05 mole), 8.1 grams of $MoO_3 \cdot H_2O$ (0.05 moles) and 10 cc of water were stirred and refluxed (ca. 140° C.) in 200 cc of xylene for 4 hours. During this time, water and xylene were removed by distillation. The reactants were freed from solid material by filtration and the filtrate stripped of volatile material by rotoevaporation. The product was a 50 wt.% mineral oil solution of a dark brown oil containing 0.886 wt.% molybdenum.

It is believed that the molybdenum-containing dispersant additives of the invention provide lubricity enhancement to lubricating oils superior to their nonmolybdized counterparts when an active sulfur donor is present and that they have utility as additives for lubricating oils providing both sludge dispersancy and lubricity enhancement.

It is to be understood that the Examples present in the foregoing specification are merely illustrative of this invention and are not intended to limit it in any manner; nor is the invention to be limited by any theory regarding its operability. The scope of the invention is to be determined by the appended claims.

What is claimed is:

1. An oil-soluble molybdenum complex of a lactone oxazoline dispersant having from 0.5 to 20 wt. % molybdenum based on the weight of said dispersant.

2. An oil-soluble molybdenum complex according to claim 1 wherein said dispersant is an oxazoline compound having an oil-solubilizing group in the form of a long chain hydrocarbon group attached to an acid group via an intermediate lactone ring so the substituted acid contains a total of 50 to 400 carbon atoms.

3. The complex according to claim 2 wherein said complex is the reaction product of a molybdenum compound with 0.5 to 1 molar equivalent of a $C_8$ to $C_{400}$ hydrocarbon substituted lactone oxazoline obtained as a reaction product of hydrocarbyl substituted lactone acid or ester, with from 1 to 1.5 molar equivalents of a 2,2-disubstituted-2-amino-1-alkanol represented by the formula

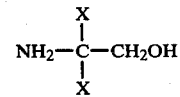

wherein X is an alkyl or hydroxy alkyl group, with at least one of the X substituents being a hydroxy alkyl group of the structure $-(CH_2)_nOH$, wherein n is 1 to 3.

4. The complex according to claim 3 wherein said molybdenum compound is of the class consisting of molybdic trioxide, ammonium thiomolybdate, ammonium bismolybdate, molybdenum halides, and ammonium heptamolybdate tetrahydrate.

5. A lubricating oil composition comprising a major proportion of mineral oil and a minor but a friction reducing amount of an oil-soluble molybdenum complex of a lactone oxazoline lubricating oil dispersant, said dispersant having from 0.5 to 20 wt. % molybdenum based on the weight of said dispersant.

6. A hydrocarbon composition comprising a major portion of a hydrocarbon and at least a friction reducing amount of the combination of: (a) a molybdenum complex of a lactone oxazoline dispersant having from 0.5 to 20 wt. % molybdenum based on the weight of said dispersant; and (b) an oil-soluble active sulfur donor, said combination providing from about 0.01 to 2.0 weight percent molybdenum and said sulfur donor being present in at least 0.25 weight percent, all of said weight percent being based on the total weight of said composition.

7. A hydrocarbon composition according to claim 6 wherein said hydrocarbon is mineral oil, said complex is oil-soluble and derived from the reaction product of one mole of a hydrocarbyl substituted lactone acid material wherein said hydrocarbyl substituent has a $(\overline{M}_n)$ ranging from 700 to 5,000 reacted with one to one and a half moles of a 2,2-disubstituted-2-amino-1-alkanol represented by the formula

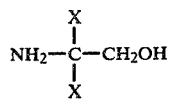

wherein X is an alkyl or hydroxy alkyl group, with at least one of the X substituents being a hydroxy alkyl group of the structure $-(CH_2)_nOH$ where n is 1 to 3, said reaction product being complexed with from 1 to 2 molar equivalents of molybdic oxide, said complex containing from 0.5 to 20 wt. % molybdenum and said sulfur donor is an oil-soluble dihydrocarbyl ester of dithiophosphoric acid.

8. A hydrocarbon composition according to claim 7 wherein said mineral oil has a viscosity as measured by ASTM-D-445 of from about 2 to 40 centistokes at 99° C., said alkanol being tris(hydroxymethyl) aminomethane and said active sulfur donor is zinc dihydrocarbyl dithiophosphate present in an amount of from 0.2 to 2 parts by weight per part by weight of said molybdenum complex which is present in an amount of from 0.02 to 1.0 wt. % based upon the total weight of said composition.

9. A concentrate comprising from 5 to 80 weight percent of the combination of an oil-soluble molybdenum complex of a lactone oxazoline dispersant having from 0.5 to 20 wt. % molybdenum based on the weight of said dispersant and from about 0.1 to 10 parts by weight of active sulfur donor per part by weight of said complex and 20 to 95 weight percent of mineral oil.

10. A method of making an oil-soluble molybdenum complex of a lactone oxazoline dispersant comprising the step of complexing a source of molybdenum with an oil-soluble lactone oxazoline dispersant in a binary solvent system comprising an aqueous component of the class consisting of water and ammonium hydroxide and a normally liquid hydrocarbon and the volume ratio of said aqueous component to said hydrocarbon component ranging from 1:1000 to 1:1.

11. A gasoline having improved antiwear properties containing from 10 to 1,000 parts per million of a molybdenum complex of a lactone oxazoline dispersant having from 0.5 to 20 wt. % molybdenum based on the weight of said dispersant.

12. A lubricating oil composition according to claim 5 wherein said dispersant has up to 10 wt. % molybdenum.

13. A lubricating oil composition according to claim 12 wherein said dispersant is borated and contains from 0.1 to 2.0 wt. % boron based on the total weight of said dispersant.

14. A hydrocarbon composition according to claim 6 wherein said hydrocarbon is mineral oil and said molybdenum complex is oil-soluble and contains from 2 to 10 wt. % molybdenum.

15. A concentrate according to claim 9 wherein said dispersant has up to 10 wt. % molybdenum.

16. A concentrate according to claim 15 wherein said dispersant is borated and contains from 0.1 to 2.0 wt. % boron.

17. The method according to claim 10 wherein said dispersant is borated and contains from 0.1 to 2.0 wt. % boron.

* * * * *